US011655198B2

(12) United States Patent
Dupuy et al.

(10) Patent No.: US 11,655,198 B2
(45) Date of Patent: *May 23, 2023

(54) PROCESS FOR THE PRODUCTION OF ISOPARAFFINIC FLUIDS WITH LOW AROMATICS CONTENT

(71) Applicant: TOTAL MARKETING SERVICES, Puteaux (FR)

(72) Inventors: Carole Dupuy, Issy les Moulineaux (FR); Katell Le Lannic Dromard, Le Havre (FR)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/481,011

(22) PCT Filed: Feb. 13, 2018

(86) PCT No.: PCT/EP2018/053471
§ 371 (c)(1),
(2) Date: Jul. 25, 2019

(87) PCT Pub. No.: WO2018/146319
PCT Pub. Date: Aug. 16, 2018

(65) Prior Publication Data
US 2020/0002626 A1 Jan. 2, 2020

(30) Foreign Application Priority Data
Feb. 13, 2017 (EP) .................................. 17155897

(51) Int. Cl.
| | |
|---|---|
| *C07C 5/13* | (2006.01) |
| *C10G 45/02* | (2006.01) |
| *C10G 45/32* | (2006.01) |
| *C10G 45/44* | (2006.01) |
| *C10G 50/00* | (2006.01) |
| *C07C 5/02* | (2006.01) |

(52) U.S. Cl.
CPC .................. *C07C 5/13* (2013.01); *C07C 5/02* (2013.01); *C10G 45/02* (2013.01); *C10G 45/32* (2013.01); *C10G 45/44* (2013.01); *C10G 50/00* (2013.01); *C10G 2300/1081* (2013.01); *C10G 2300/1088* (2013.01); *C10G 2300/301* (2013.01); *C10G 2300/4006* (2013.01); *C10G 2300/4012* (2013.01); *C10G 2300/4018* (2013.01)

(58) Field of Classification Search
CPC .................................. C07C 5/02; C07C 5/13
See application file for complete search history.

(56) References Cited

U.S. PATENT DOCUMENTS

| | | | |
|---|---|---|---|
| 5,800,816 A | 9/1998 | Brieva | |
| 5,882,663 A | 3/1999 | Koeniger | |
| 9,688,924 B2 | 6/2017 | Dalemat et al. | |
| 2005/0080304 A1 | 4/2005 | Lehtonen | |
| 2005/0288471 A1 | 12/2005 | Bitterlich et al. | |
| 2008/0193404 A1* | 8/2008 | Lange .................. | A61K 8/31 424/70.11 |
| 2012/0264656 A1* | 10/2012 | Germanaud .......... | A61Q 19/00 507/103 |
| 2016/0289573 A1 | 10/2016 | Dupuy | |
| 2016/0312131 A1 | 10/2016 | Luebke et al. | |
| 2018/0148656 A1 | 5/2018 | Germanaud et al. | |
| 2018/0155636 A1 | 6/2018 | Germanaud et al. | |

FOREIGN PATENT DOCUMENTS

| | | | | |
|---|---|---|---|---|
| DE | 102004018752 A1 * | 11/2005 | .............. | C09D 7/20 |
| PL | 199805 B1 * | 11/2008 | | |
| WO | 2013093227 | 6/2013 | | |

OTHER PUBLICATIONS

Wypych, George "Isododecane" Knovel Solvents—A Properties Database. 2008. pp. 1-2 (Year: 2008).*
Machine translation WO 2013/093227. published Jun. 27, 2013. retrieved Jun. 19, 2020. (Year: 2013).*
Machine translation DE 102004018752. Retrieved Jan. 19, 2021 (Year: 2021).*
Machine translation PL 199805. Obtained May 25, 2022 (Year: 2022).*
Johnson, W., et al., "Safety Assessment of Isoparaffins as Used in Cosmetics," International Journal of Toxicology, U.S., 2012, vol. 31, No. 6_supp, p. 269S-p. 273S.

* cited by examiner

*Primary Examiner* — Philip Y Louie
*Assistant Examiner* — Alyssa L Cepluch
(74) *Attorney, Agent, or Firm* — Duane Morris LLP; Gregory M. Lefkowitz; Brandon A. Chan

(57) ABSTRACT

The invention provides a process for preparing a fluid having a boiling point in the range of from 150 to 260° C. and comprising more than 80% by weight of isoparaffins and less than 50 ppm of aromatics, comprising the step of catalytically hydrogenating a feed comprising more than 85% by weight of oligomerized olefins, at a temperature from 115 to 195° C. and at a pressure from 30 to 70 bars. The invention also provides the fluid obtainable by the process of the invention and the use of said fluid.

15 Claims, No Drawings

PROCESS FOR THE PRODUCTION OF ISOPARAFFINIC FLUIDS WITH LOW AROMATICS CONTENT

CROSS-REFERENCE TO RELATED APPLICATIONS

This application is a § 371 national stage entry of International Application No. PCT/EP2018/053471, filed Feb. 13, 2018, which claims priority to European Application No. 17155897.6, filed Feb. 13, 2017, the entire contents of which are incorporated herein by reference.

FIELD OF THE INVENTION

The invention relates to the production of isoparaffinic fluids having a narrow boiling range and having a very low aromatic content and their uses. The invention relates to a process for producing these isoparaffinic fluids by hydrogenation of olefinic feedstocks.

BACKGROUND ART

Hydrocarbon fluids find widespread use as solvents such as in adhesives, cleaning fluids, explosives solvents, for decorative coatings and printing inks, light oils for use in applications such as metal extraction, metalworking or demoulding and industrial lubricants, and drilling fluids. The hydrocarbon fluids can also be used as extender oils in adhesives and sealant systems such as silicone sealants and as viscosity depressants in plasticised polyvinyl chloride formulations and as carrier in polymer formulation used as flocculants for example in water treatment, mining operations or paper manufacturing and also used as thickener for printing pastes. Hydrocarbon fluids may also be used as solvents in a wide variety of other applications such as chemical reactions.

The chemical nature and composition of hydrocarbon fluids varies considerably according to the use to which the fluid is to be put. Important properties of hydrocarbon fluids are the distillation range generally determined by ASTM D-86 or the ASTM D-1160 vacuum distillation technique used for heavier materials, flash point, density, aniline point as determined by ASTM D-611, aromatic content, sulphur content, viscosity, colour and refractive index.

These fluids tend to have narrow boiling point ranges as indicated by a narrow range from Initial Boiling Point (IBP) to Final Boiling Point (FBP) according to ASTM D-86. The Initial Boiling Point and the Final Boiling Point will be chosen according to the use to which the fluid is to be put. However, the use of the narrow cuts provides the benefit of a narrow flash point which is important for safety reasons. The narrow cut also brings important fluid properties such as a better defined aniline point or solvency power, then viscosity, and defined evaporation conditions for systems where drying is important, and finally better defined surface tension.

To produce these specific fluids, the preferred feedstocks are usually specific gasoil cuts, such as low sulphur feed. A typical feed could be hydrocraked vacuum gasoil (VGO) for example.

WO201161575 discloses a process for hydrogenating a low sulphur feed typically a hydrocracked vacuum gasoil into very low aromatic hydrocarbon fluids.

Other type of feedstock can be used to produce these specific fluids such as hydrocarbon cut originating from a gas-to-liquid process, hydrodeoxygenated hydrocarbon cut obtained from biomass or a gas condensate.

WO2015/071160 discloses a hydrogenation process of a hydrocarbon feedstock originating from a gas to liquid process in blend to produce low aromatics fluids.

WO2016/185046 and EP3095839 disclose a hydrogenation process of a hydrodeoxygenated isomerized hydrocarbon cut obtained from biomass.

There is still a need to produce these particular fluids with low aromatics content and specific properties such as aniline point, solvency power and defined boiling range with others available feedstock.

One aim of the invention is to provide a process for preparing specific hydrocarbon fluids, which process does not require using hydrocracked vacuum gasoil (HCVGO) as a feed.

US2016/0312131 discloses a process for the production of jet-range hydrocarbons. The process of this document involves one or several dilution steps. US2016/0312131 does not disclose a step of hydrogenation of a feed comprising more than 90% by weight of oligomerized olefins.

WO2013/093227 discloses a process for producing middle distillates starting from atmospheric residuum or vacuum gasoil. This document does not disclose a fluid having a boiling point in the range of from 150 to 230° C. and comprising more than 80% of isoparaffins and less than 50 ppm of aromatics.

The invention also provides new hydrocarbon isoparaffinic fluids, and especially obtainable by the process of the invention.

Another object of the invention is the use of the improved fluids as industrial solvents cleaning solvent, solvent for resins, adhesive, solvent for polymerization, printing ink, metal working fluid, cutting fluid, rolling oil, EDM fluid, coating fluid and paint composition, cupping, protection fluid, hand soap, household product, aerosol, product for photocopiers, odorless fuel for oil stoves, fluid intended for the cosmetic formulations.

SUMMARY OF THE INVENTION

The invention provides a process for preparing a fluid having a boiling point in the range of from 150 to 260° C., preferably from 150 to 230° C., and comprising more than 80% by weight of isoparaffins and less than 50 ppm of aromatics, comprising the step of catalytically hydrogenating a feed comprising more than 85% by weight, preferably more than 90% by weight of oligomerized olefins, at a temperature from 115 to 195° C. and at a pressure from 30 to 70 bars.

According to one embodiment, the process comprises three hydrogenation stages, preferably in three separate reactors.

According to an embodiment, the hydrogenation conditions are the following:
Pressure: 40 to 60 bars, and preferably at about 50 bars;
Temperature: 125 to 185° C. and preferably 135 to 175° C.;
Liquid hourly space velocity (LHSV): 0.1 to 3 $hr^{-1}$, preferably 0.2 to 2 $hr^{-1}$, and most preferably 0.3 to 1 $hr^{-1}$;
Hydrogen treat rate: 50 to 300 $Nm^3$/ton of feed, preferably 60 to 200 $Nm^3$/ton of feed and most preferably 80 to 130 $Nm^3$/ton of feed.

According to another embodiment, the feed comprises more than 90% by weight of oligomerized olefins, most preferably more than 95% by weight of oligomerized olefins.

According to another embodiment, the oligomerized olefinic feed is selected from the group consisting of: trimeric butene (also named trimeric butylene) and tetrameric propylene (also named tetrameric propene) cuts.

According to another embodiment, the oligomerized olefinic feed comprises a majority of $C_{12}$ olefins.

According to another embodiment, the process comprises (i) a fractionating step carried out before the hydrogenating step, or after the hydrogenating step or both, or (ii) the process comprises three hydrogenation stages, preferably in three separate reactors, or (iii) both (i) and (ii).

According to another embodiment, the fluid has a boiling point in the range of from 170 to 220° C., preferably from 180 to 210° C., and/or a boiling range below 90° C., preferably below 80° C., more preferably not more than 60° C., even more preferably not more than 40° C., advantageously from 10 to 20° C.

According to another embodiment, the fluid contains more than 90% by weight of paraffins, preferably more than 93% by weight of paraffins and even more preferably more than 97% by weight of paraffins.

According to another embodiment, the fluid contains more than 80% by weight of isoparaffins, preferably more than 85% by weight of isoparaffins and more preferably more than 90% by weight of isoparaffins.

According to another embodiment, the fluid contains less than 10% by weight of normal paraffins, preferably less than 8% by weight of normal paraffins and more preferably less than 5% by weight of normal paraffins.

According to another embodiment, the fluid contains less than 50 ppm of aromatics by weight, preferably less than 20 ppm by weight, more preferably less than 10 ppm by weight.

According to another embodiment, the fluid contains less than 10% by weight of naphthens, preferably less than 7% by weight and advantageously less than 3% by weight.

According to another embodiment, the fluid thus produced has:
- a naphthenic content below 10% by weight, especially below 7% and even below 3%, and/or
- an isoparaffinic content above 80% by weight, especially above 85%, and even above 90%, and/or
- a normal paraffinic content below 10% by weight, especially below 8% and even below 5%, and/or
- a boiling point in the range of from 150 to 260° C., preferably from 150 to 230° C. according to ASTM D86, preferably from 170 to 220° C. and more preferably from 180 to 210° C., and/or
- a brome index of less than 5, preferably less than 2, more preferably less than 1 mgBr/100 g of fluid.

The invention also provides the fluid obtainable by the process of the invention.

The invention also provides the use of said fluid as industrial solvent, cleaning solvent, solvent for resins, adhesive, solvent for polymerization, printing ink, metal working fluid, cutting fluid, rolling oil, EDM fluid, coating fluid and paint composition, cupping, protection fluid, hand soap, household product, aerosol, product for photocopiers, odorless fuel for oil stoves, fluid intended for the cosmetic formulations.

DESCRIPTION OF EMBODIMENTS OF THE INVENTION

The invention relates to a process for preparing a fluid having a boiling point in the range of from 150 to 260° C., preferably from 150 to 230° C. and comprising more than 80% of isoparaffins and less than 50 ppm of aromatics, comprising the step of catalytically hydrogenating a feed comprising more than 85% by weight, preferably more than 90% by weight, of oligomerized olefins, at a temperature from 115 to 195° C. and at a pressure from 30 to 70 bars.

The process of the invention allows preparing isoparaffinic fluids very suitable for various industrial applications.

The process of the invention allows preparing in particular isoparaffinic fluids with specific characteristics in term of boiling point, aromatic and isoparaffin contents, solvency power and viscosity.

The feedstock will first be disclosed, then the hydrogenation step and the associated fractionating step, and finally the fluids.

Feedstock

The feedstock or simply feed is a feed which is the result of a process of oligomerization of olefins, as practised in the petrochemical field.

The oligomerization process applied transforms olefins contained in light cracked cuts into heavier olefins containing more than 6 carbon atoms (also called C6+ olefins).

Various oligomerization processes are discloses in the literature. Most of these processes are for production of iso-olefins oligomers.

US2005/0288471 discloses a process for the production of oligomers of 1- or 2-butane, in particular octenes and dodecenes, from a hydrocarbon stream consisting of branched and linear hydrocarbon compounds having 4 carbon atoms and comprising olefinic branched and linear hydrocarbon compounds having 4 carbon atoms. This process enables the preparation of substantially unbranched octene and dodecene from a fraction comprising both linear and branched olefinic hydrocarbon compounds having 4 carbon atoms.

In the Polynaptha™ process developed by Axens, propylene and/or mixed butenes are catalytically oligomerized in a series of fixed bed reactors. Conversion and selectivity are controlled by reactor temperature adjustment while the heat of reaction is removed by feed-effluent heat exchange and intermediate reactor cooling. The reactor section effluent is fractionated producing LPG raffinate, gasoline and middle distillate fractions such as kerosene or diesel. This technology is well suited for revamping existing phosphoric acid polymerization units.

Another possible process for the production of olefins is the Selectopol™ process from Axens. This process is a variant of the Polynaphtha™ process using the same catalyst but at lower severity.

Light olefin conversion ranges typically from 90 to 99% depending on feedstock quality and product distribution.

Such feed is also called olefinic cut. The olefinic cut used as feed for the process of the invention contains less than 5% by weight of paraffins, preferably less than 2% and more preferably less than 1%.

The olefinic cut used as feed for the process of the invention contains more than 90% by weight of olefins, preferably more than 92%, more preferably more than 95% measured according to ASTM D1319.

The feed typically contains less than 2 ppm by weight of sulphur, preferably less than 1 ppm by weight and more preferably less than 0.5 ppm by weight measured according to NF M 07059.

The feed typically contains also less than 10% by weight of aromatics, preferably less than 8% and more preferably less than 5% measured by HPLC (EN ISO 12916).

The feed typically has a boiling point in the range of from 170 to 280° C., preferably from 180 to 250° C. and more preferably from 180 to 220° C. according to EN ISO 3405.

Typically, the feed shall have a density at 15° C. lower than or equal to 0.800 g/cm$^3$ as measured according to method ASTM D4052.

According to one embodiment, the feed shall have a density lower or equal to 0.800 g/cm$^3$ as measured according to method ASTM D4052, and it should consist mostly of an olefinic cut with a boiling point in the range of from 170 to 280° C.

According to another embodiment, the feed contains less than 2 ppm by weight of sulphur and less than 10% of aromatics. Preferably, the feed contains less than 1 ppm by weight of sulphur and less than 8% of aromatics. More preferably, the feed contains less than 0.5 ppm of sulphur and less than 5% of aromatics.

According to another embodiment, the feed contains less than 5% by weight of paraffins, more than 90% of olefins and less than 10% of aromatics. Preferably, the feed contains less than 2% by weight of paraffins, more than 92% of olefins and less than 8% of aromatics. More preferably the feed contains less than 1% by weight of paraffins, more than 95% of olefins and less than 5% of aromatics.

According to another embodiment, the feed consists of an olefinic cut comprising a majority of $C_{12}$ olefins.

According to another embodiment, the feed consists of an olefinic cut comprising a majority of branched (iso) $C_{12}$ olefins According to another embodiment, the feed consists of an olefinic cut comprising a majority of branched (iso) $C_{12}$ olefins chosen amongst trimeric butene cuts and tetrameric propylene cuts.

According to another embodiment, the feed consists of an olefinic cut comprising a majority of branched (iso) $C_{12}$ olefins chosen from a trimeric butene cut with a boiling range from 170 to 220° C.

According to another embodiment, the feed consists of an olefinic cut comprising a majority of branched (iso) $C_{12}$ olefins chosen from a tetrameric propylene cut with a boiling range from 150 to 260° C.

Preferably, within the meaning of the present invention, the expression "a majority of" means "more than 50% by weight, preferably at least 70% by weight, more preferably at least 90% by weight, even more preferably at least 95% by weight".

Hydrogenation Step

The feedstock issued from the oligomerization of olefins is then hydrogenated. Preferably the feedstock issued from the oligomerization of olefins is a trimeric butene cut and ideally a tri-n-butene cut comprising a majority of 12 carbon atoms olefins. The feedstock can optionally be pre-fractionated.

The hydrogenation step allows the conversion of olefins to paraffins and the elimination of almost all the aromatics compounds. The process of the invention is particularly efficient to convert the normal and/or iso olefin cut into low aromatics isoparaffinic fluids.

Hydrogen that is used in the hydrogenation unit is typically a high purity hydrogen, e.g. with a purity of more than 99%, albeit other grades can be used.

Hydrogenation takes place in one or more reactors. The reactor can comprise one or more catalytic beds. Catalytic beds are usually fixed beds.

Hydrogenation takes place using a catalyst. Typical hydrogenation catalysts include but are not limited to: nickel, platinum, palladium, rhenium, rhodium, nickel tungstate, nickel molybdenum, molybdenum, cobalt molybdenate, nickel molybdenate on silica and/or alumina carriers or zeolites. A preferred catalyst is Ni-based and is supported on an alumina carrier, having a specific surface area varying from 100 to 200 m$^2$/g of catalyst.

The hydrogenation conditions are typically the following:
Pressure: 30 to 70 bars, preferably 40 to 60 bars, and most preferably at about 50 bars;
Temperature: 115 to 195° C., preferably 125 to 185° C. and most preferably 135 to 175° C.;
Liquid hourly space velocity (LHSV): 0.1 to 3 hr$^{-1}$, preferably 0.2 to 2 hr$^{-1}$, and most preferably 0.3 to 1 hr$^{-1}$;
Hydrogen treat rate: 50 to 300 Nm$^3$/ton of feed, preferably 60 to 200 Nm$^3$/ton of feed and most preferably 80 to 130 Nm$^3$/ton of feed.

The temperature in the reactors can be typically about 150-160° C. and the pressure can be typically about 50 bars while the liquid hourly space velocity can be typically about 0.6 and the treat rate can be typically about 80 to 130 Nm$^3$/ton of feed, depending on the feed quality.

The hydrogenation process of the invention can be carried out in several stages. There can be two or three stages, preferably three stages, preferably in three separate reactors. The first stage will operate the sulphur trapping, hydrogenation of substantially all unsaturated compounds, and up to about 90% of hydrogenation of aromatics. The flow exiting from the first reactor contains substantially no sulphur. In the second stage the hydrogenation of the aromatics continues, and up to 99% of aromatics are hydrogenated. The third stage is a finishing stage, allowing an aromatic content as low as 300 ppm or even less such as below 100 ppm or even below 50 ppm. The third stage may allow reducing the brome index of the fluid to a value of less than mgBr/100 g of fluid or even less such as below 2 or even below 1 mgBr/100 g of fluid.

The catalysts can be present in varying or substantially equal amounts in each reactor, e.g. for three reactors according to weight amounts of 0.05-0.5/0.10-0.70/0.25-0.85, preferably 0.07-0.25/0.15-0.35/0.4-0.78 and most preferably 0.10-0.20/0.20-0.32/0.48-0.70.

It is also possible to have two hydrogenation reactors instead of three.

It is also possible that the first reactor be made of twin reactors operated alternatively in a swing mode. This may be useful for catalyst charging and discharging: since the first reactor comprises the catalyst that is poisoned first (substantially all the sulphur is trapped in and/or on the catalyst) it should be changed often.

One reactor can be used, in which two, three or more catalytic beds are installed.

It may be necessary to insert quenches on the recycle to cool effluents between the reactors or catalytic beds to control reaction temperatures and consequently hydrothermal equilibrium of the hydrogenation reaction. In a preferred embodiment, there is no such intermediate cooling or quenching.

In an embodiment the resulting product and/or separated gas is/are at least partly recycled to the inlet of the hydrogenation stages. This dilution helps maintaining the exothermicity of the reaction within controlled limits, especially at the first stage. Recycling also allows heat-exchange before the reaction and also a better control of the temperature.

The stream exiting the hydrogenation unit contains the hydrogenated product and hydrogen. Flash separators are used to separate effluents into gas, mainly remaining hydrogen, and liquids, mainly hydrogenated hydrocarbons. The process can be carried out using three flash separators, one of high pressure, one of medium pressure, and one of low pressure, very close to atmospheric pressure.

The hydrogen gas that is collected on top of the flash separators can be recycled to the inlet of the hydrogenation unit or at different levels in the hydrogenation units between the reactors.

The fractionation stage can be carried out at about atmospheric pressure, or it can be carried out under vacuum pressure that is at about from 10 to 50 mbars, more preferably from 20 to 40 mbars, even more preferably at about 30 mbars.

The fractionation stage can be operated such that various hydrocarbon fluids can be withdrawn simultaneously from the fractionation column, and the boiling range of which can be predetermined.

Therefore, fractionation can take place before hydrogenation, after hydrogenation, or both.

The hydrogenation reactors, the separators and the fractionation unit can thus be connected directly, without having to use intermediate tanks. By adapting the feed, especially the initial and final boiling points of the feed, it is possible to produce directly, without intermediate storage tanks, the final products with the desired initial and final boiling points. Moreover, this integration of hydrogenation and fractionation allows an optimized thermal integration with reduced number of equipment and energy savings.

Fluids of the Invention

The fluids of the invention, produced according to the process of the invention possess outstanding properties, in terms of aniline point or solvency power, molecular weight, vapour pressure, viscosity, defined evaporation conditions for systems where drying is important, and defined surface tension. Moreover the fluids of the invention are odourless and have a low pour point.

The fluids resulting of the hydrogenating process of the invention are isoparaffinic fluids with very low aromatics content.

Typically, the isoparaffinic fluids of the invention comprise from 11 to 13 carbon atoms, preferably 12 carbon atoms.

The isoparaffinic fluids of the invention have a boiling point in the range of from 150 to 260° C. according to ASTM D86, preferably from 150° C. to 230° C., more preferably from 170 to 220° C. and even more preferably from 180 to 210° C. and also exhibit an enhanced safety, due to the very low aromatics content.

The boiling range of the improved fluids is preferably not more than 90° C., preferably not more than 80° C., more preferably not more than 60° C., even more preferably not more than 40° C., advantageously from 10 to 20° C.

The fluids of the invention are paraffinic fluids. They contain typically more than 90% by weight of paraffins, preferably more than 93% by weight of paraffins and even more preferably more than 97% by weight of paraffins, as measured by gas chromatography GC.

The fluids of the invention are primarily isoparaffinic and contain more than 80% by weight of isoparaffins, preferably more than 85% by weight of isoparaffins and more preferably more than 90% by weight of isoparaffins measured by GC. These fluids can be qualified as isoparaffinic fluids.

The fluids of the invention contain less than 10% by weight of normal paraffins, preferably less than 8% by weight of normal paraffins and more preferably less than 5% by weight of normal paraffins measured by GC.

The fluids of the invention contain less than 10% by weight of naphthens, preferably less than 7% by weight of naphthens and more preferably less than 3% by weight of naphthens measured by GC.

The isoparaffinic fluids of the invention or simply the fluids of the invention typically contain less than 50 ppm by weight of aromatics measured by UV spectrometry, more preferably less than 20 ppm, and even more preferably less than 10 ppm. This makes them suitable for use in construction fluids compositions as well as in industrial products.

According to one embodiment the isoparaffinic fluids of the invention contain more than 80% by weight of isoparaffins, less than 10% by weight of naphthens and less than 50 ppm of aromatics. Preferably, the isoparaffinic fluids of the invention contain more than 85% by weight of isoparaffins, less than 7% by weight of naphthens and less than 20 ppm of aromatics. More preferably, the isoparaffinic fluids of the invention contain 90% by weight of isoparaffins, less than 3% by weight of naphthens and less than 10 ppm of aromatics.

According to a second embodiment the isoparaffinic fluids of the invention contain more than 80% by weight of isoparaffins, less than 10% by weight of normal paraffins, less than 10% by weight of naphthens and less than 50 ppm of aromatics. Preferably, the isoparaffinic fluids of the invention contain more than 85% by weight of isoparaffins, less than 8% by weight of normal paraffins, less than 7% of by weight naphthens and less than 20 ppm of aromatics. More preferably, the isoparaffinic fluids of the invention contain 90% by weight of isoparaffins, less than 5% by weight of normal paraffins, less than 3% by weight of naphthens and less than 10 ppm of aromatics.

According to another embodiment the isoparaffinic fluids of the invention contain more than 80% by weight of isoparaffins, less than 10% by weight of normal paraffins, less than 10% by weight of naphthens, less than 50 ppm of aromatics and have a boiling point in the range of from 150 to 260° C., preferably from 150 to 230° C. Preferably, the isoparaffinic fluids of the invention contain more than 85% by weight of isoparaffins, less than 8% by weight of normal paraffins, less than 7% by weight of naphthens, less than 20 ppm of aromatics and have a boiling point in the range of from 170 to 220° C. More preferably, the isoparaffinic fluids of the invention contain 90% by weight of isoparaffins, less than 5% by weight of normal paraffins, less than 3% by weight of naphthens, less than 10 ppm of aromatics and have a boiling point in the range of from 180 to 210° C.

The isoparaffinic fluids of the invention also have extremely low sulphur content, typically less than 5 ppm by weight, even less than 3 ppm and preferably less than 1 ppm, at a level too low to be detected by the usual low-sulphur analyzers.

The isoparaffinic fluids of the invention also have an aniline point from 70 to 90° C., preferably from 75 to 85° C., more preferably at 82° C. according to ISO 2977.

The isoparaffinic fluids of the invention also have a pour point below −50° C., preferably below −60° C. according to ASTM D97.

The isoparaffinic fluids of the invention also have preferably a brome index of less than 5, preferably less than 2, more preferably less than 1 mgBr/100 g of fluid, according to ASTM D 2710.

All percentages and ppm are by weight unless indicated to the contrary. Singular and plural are used interchangeably to designate the fluid(s).

These characteristics make them suitable for large variety of uses for example, industrial solvents, cleaning solvents, solvents for resins, adhesives, solvents for polymerization, printing inks, metal working fluids, cutting fluids, rolling oils, EDM fluids (electro discharge machining), coating fluids and paint compositions, cupping, protection fluids, hand soaps, household products, aerosols, products for photocopiers, odorless fuels for oil stoves, fluids intended for the cosmetic formulations.

In all this foreseen uses, the Initial Boiling Point to Final Boiling Point ranges are selected according to the particular use and composition.

The isoparaffinic nature of the improved fluids allows for improved low temperature properties. The isoparaffinic fluids of the invention may also be used as new and improved solvents, particularly as solvents for resins, adhesives and solvents for polymerization. The solvent-resin composition may comprise a resin component dissolved in the fluid, the fluid comprising 5 to 95% by total volume of the composition.

The improved fluids may be used in place of solvents currently used for inks, coatings and the like.

The improved fluids may also be used to dissolve resins such as: acrylic-thermoplastic, acrylic-thermosetting, chlorinated rubber, epoxy (either one or two part), hydrocarbon (e.g., olefins, terpene resins, rosin esters, petroleum resins, coumarone-indene, styrene-butadiene, styrene, methyl-styrene, vinyl-toluene, polychloroprene, polyamide, polyvinyl chloride and isobutylene), phenolic, polyester and alkyd, polyurethane and modified polyurethane, silicone and modified silicone (MS polymers), urea, and, vinyl polymers and polyvinyl acetate.

Examples of the type of specific applications for which the improved fluids and fluid-resin blends may be used include coatings, cleaning compositions and inks. For coatings the blend preferably has high resin content, i.e., a resin content of 20% to 80% by volume. For inks, the blend preferably contains a lower concentration of the resin, i.e., 5%-30% by volume.

In yet another embodiment, various pigments or additives may be added.

The improved fluids can be used as cleaning compositions for the removal of hydrocarbons.

The improved fluids may also be used in cleaning compositions such as for use in removing ink, more specifically in removing ink from printing.

In the offset printing industry it is important that ink can be removed quickly and thoroughly from the printing surface without harming the metal or rubber components of the printing machine. Further there is a tendency to require that the cleaning compositions are environmentally friendly in that they contain no or hardly any aromatic volatile organic compounds and/or halogen containing compounds. A further trend is that the compositions fulfil strict safety regulations. In order to fulfil the safety regulations, it is preferred that the compositions have a flash point of more than 60° C., more preferably a flash point more than 63° C., even more preferably a flash point of more than 67° C. and even more preferably a flash point of more than 70° C. This makes them very safe for transportation, storage and use. The improved fluids have been found to give a good performance in that ink is readily removed while these requirements are met.

All amounts are given by weight, unless indicated to the contrary.

EXAMPLES

The following examples illustrate the invention without limiting it.

Example 1

The aim of the present example is to describe the preparation of hydrocarbon fluids according to the process of the present invention.

In the present invention, a commercial trimeric butene feedstock, typically a C12-centered iso-olefinic cut, was hydrogenated in presence of a nickel hydrogenating catalyst according to the process of the invention under a pressure of 50 bars, at a liquid hourly space velocity (LHSV) of 0.6 h$^{-1}$ and at a temperature from 135 to 175° C.

The table 1 shows the characteristics of the trimeric n-butene feedstock.

TABLE 1

| Analyses | Normes | Unit | Values |
|---|---|---|---|
| Density at 15° C. | EN ISO 12185 | kg/m$^3$ | 771.0 |
| Aromatic content | HPLC (EN ISO 12916) | % | <5 |
| Paraffinic content | FIA ASTM D1319 | % | <0.3 |
| Olefin content | FIA ASTM D1319 | % | >95 |
| Bromine number | ASTN D 1159 | g Br2/100 g | 98.0 |
| Sulfur content | NF M 07059 | ppm | 0.1 |
| Distillation D86 | Normes | Unités | |
| Initial Point | EN ISO 3405 | ° C. | 192.2 |
| 2% Point | EN ISO 3405 | ° C. | 195.3 |
| 5% Point | EN ISO 3405 | ° C. | 195.6 |
| 10% Point | EN ISO 3405 | ° C. | 195.7 |
| 20% Point | EN ISO 3405 | ° C. | 196.0 |
| 30% Point | EN ISO 3405 | ° C. | 196.2 |
| 40% Point | EN ISO 3405 | ° C. | 196.4 |
| 50% Point | EN ISO 3405 | ° C. | 196.6 |
| 60% Point | EN ISO 3405 | ° C. | 196.9 |
| 65% Point | EN ISO 3405 | ° C. | 197.1 |
| 70% Point | EN ISO 3405 | ° C. | 197.2 |
| 80% Point | EN ISO 3405 | ° C. | 197.8 |
| 90% Point | EN ISO 3405 | ° C. | 198.9 |
| 95% Point | EN ISO 3405 | ° C. | 200.6 |
| Dry Point | EN ISO 3405 | ° C. | 205.4 |

The hydrogenation process is carried out and the hydrogenated cut is then fractionated into different cuts, the main one showing the characteristics given in table 2 hereafter.

TABLE 2

| Analyses | Norms | Unity | Isoparaffinic hydrogenated distillate |
|---|---|---|---|
| Density at 15° C. | EN ISO 12185 | kg/m$^3$ | 768.0 |
| Appearance | VISUAL | — | clear & bright |
| Saybolt Colour | NF M 07-003 | — | 30 |
| Refractive index at 20° C. | ASTM D 1218 | — | 1.4278 |
| Pensky-Martens Flash Point | EN ISO 2719 | ° C. | 70.5 |
| Viscosity at 20° C. | EN ISO 3104 | mm2/s | 1.754 |
| Viscosity at 40° C. | EN ISO 3104 | mm2/s | 1.285 |
| Aniline Point | ISO 2977 | ° C. | 79.3 |
| Paraffinic content | GC | % | 97.34 |
| Iso-paraffin content | GC | % | 94.25 |
| Normal paraffin content | GC | % | 3.09 |
| Naphtenic content | GC | % | 2.66 |
| Aromatic content | UV spectrometry | ppm | 8 |
| Brome Index | ASTM D 2710 | mgBr/100 g | 0 |

TABLE 2-continued

| Analyses | Norms | Unity | Isoparaffinic hydrogenated distillate |
|---|---|---|---|
| Benzene content | ASTM D 6229 | ppm | 0 |
| Sulfur content | NF M 07059 | ppm | <0.1 |
| Distillation D86 | — | — | — |
| Initial Point | EN ISO 3405 | ° C. | 192.3 |
| 2% Point | EN ISO 3405 | ° C. | 194.2 |
| 5% Point | EN ISO 3405 | ° C. | 194.6 |
| 10% Point | EN ISO 3405 | ° C. | 194.8 |
| 20% Point | EN ISO 3405 | ° C. | 195.1 |
| 30% Point | EN ISO 3405 | ° C. | 195.3 |
| 40% Point | EN ISO 3405 | ° C. | 195.5 |
| 50% Point | EN ISO 3405 | ° C. | 195.7 |
| 60% Point | EN ISO 3405 | ° C. | 195.8 |
| 65% Point | EN ISO 3405 | ° C. | 195.9 |
| 70% Point | EN ISO 3405 | ° C. | 196.1 |
| 80% Point | EN ISO 3405 | ° C. | 196.5 |
| 90% Point | EN ISO 3405 | ° C. | 197.6 |
| 95% Point | EN ISO 3405 | ° C. | 200.2 |
| Dry Point | EN ISO 3405 | ° C. | 206.8 |

The results show that the properties of the product according to the invention make it very suitable for hydrocarbon fluid applications. These results show that the product prepared according to the process of the invention is free of sulphur and exhibits a very low aromatic content, and is isoparaffinic in nature.

Example 2

A tetrameric propylene feedstock, typically a C12-centered iso-olefinic cut, was hydrogenated with the same experimental conditions as the trimeric butylene cut feedstock in example 1.

Table 3 shows the characteristics of the tetrameric propylene feedstock.

TABLE 3

| Analyses | Norms | Unit | Values |
|---|---|---|---|
| Density at 15° C. | EN ISO 12185 | kg/m$^3$ | 777.2 |
| Aromatic content | HPLC (EN ISO 12916) | % | <5 |
| Paraffinic content | FIA ASTM D1319 | % | <0.3 |
| Olefin content | FIA ASTM D1319 | % | >95 |
| Bromine Number | ASTM D 2710 | gBr$_2$/100 g | 95 |
| Sulfur content | NF M 07059 | ppm | 0.1 |
| Distillation D86 | | | |
| Initial Point | EN ISO 3405 | ° C. | 174.5 |
| 1% Point | EN ISO 3405 | ° C. | 178.3 |
| 2% Point | EN ISO 3405 | ° C. | 180.0 |
| 5% Point | EN ISO 3405 | ° C. | 183.1 |
| 10% Point | EN ISO 3405 | ° C. | 185.6 |
| 20% Point | EN ISO 3405 | ° C. | 188.9 |
| 30% Point | EN ISO 3405 | ° C. | 192.0 |
| 40% Point | EN ISO 3405 | ° C. | 195.2 |
| 50% Point | EN ISO 3405 | ° C. | 198.1 |
| 60% Point | EN ISO 3405 | ° C. | 201.5 |
| 65% Point | EN ISO 3405 | ° C. | 203.4 |
| 70% Point | EN ISO 3405 | ° C. | 205.6 |
| 80% Point | EN ISO 3405 | ° C. | 211.8 |
| 90% Point | EN ISO 3405 | ° C. | 223.9 |
| 95% Point | EN ISO 3405 | ° C. | 234.3 |
| Dry Point | EN ISO 3405 | ° C. | 252.7 |

The hydrogenation process is carried out and the hydrogenated cut is then fractionated into different cuts, the main one showing the characteristics given in table 4 hereafter.

TABLE 4

| Analyses | Norms | Unit | Isoparaffinic hydrogenated distillate |
|---|---|---|---|
| Density at 15° C. | EN ISO 12185 | kg/m$^3$ | 768.9 |
| Appearance | Visual | — | Clear & bright |
| Saybolt Colour | NF M 07-003 | — | 30 |
| Pensky-Martens Flash Point | EN ISO 2719 | ° C. | 67.0 |
| Aromatic content | HPLC (EN ISO 12916) | ppm | 5 |
| Brome index | ASTM D 2710 | mgBr/100 g | 0 |
| Benzene content | ASTM D 6229 | Ppm | 0 |
| Sulfur content | NF M 07059 | ppm | 0.1 |
| Distillation D86 | | | |
| Initial Point | EN ISO 3405 | ° C. | 173.5 |
| 1% Point | EN ISO 3405 | ° C. | 178.7 |
| 2% Point | EN ISO 3405 | ° C. | 180.8 |
| 5% Point | EN ISO 3405 | ° C. | 183.9 |
| 10% Point | EN ISO 3405 | ° C. | 186.7 |
| 20% Point | EN ISO 3405 | ° C. | 190.4 |
| 30% Point | EN ISO 3405 | ° C. | 193.8 |
| 40% Point | EN ISO 3405 | ° C. | 196.9 |
| 50% Point | EN ISO 3405 | ° C. | 200.0 |
| 60% Point | EN ISO 3405 | ° C. | 203.4 |
| 65% Point | EN ISO 3405 | ° C. | 205.6 |
| 70% Point | EN ISO 3405 | ° C. | 207.8 |
| 80% Point | EN ISO 3405 | ° C. | 214.5 |
| 90% Point | EN ISO 3405 | ° C. | 227.6 |
| 95% Point | EN ISO 3405 | ° C. | 239.3 |
| Dry Point | EN ISO 3405 | ° C. | 257.1 |

The results show that the properties of the product according to the invention make it very suitable for hydrocarbon fluid applications. These results show that the product prepared according to the process of the invention is free of sulphur and exhibits a very low aromatic content, and is isoparaffinic in nature.

The invention claimed is:

1. A method for the preparation of a fluid having an initial boiling point and a final boiling point in the range of from 150 to 260° C. and comprising more than 80% by weight of isoparaffins and less than 50 ppm of aromatics and having a bromine index of less than 1 mg/Br/100 g of fluid, comprising the step of catalytically hydrogenating a feed comprising more than 85% by weight of oligomerized olefins, at a temperature from 115 to 195° C. at a pressure from 30 to 70 bar, and at a liquid hourly space velocity (LHSV) from 0.1 to 3.0 hr$^{-1}$, wherein the method comprises three hydrogenation stages in three separate reactors, wherein the oligomerized olefinic feed is selected from tetrameric propylene cuts.

2. The method of claim 1, wherein the hydrogenation conditions are the following:
Pressure: 40 to 60 bars;
Temperature: 125 to 185° C.;
Liquid hourly space velocity (LHSV): 0.1 to 1.0 hr$^{-1}$;
Hydrogen treat rate: 50 to 300 Nm$^3$/ton of feed.

3. The method of claim 1, wherein the feed comprises more than 90% by weight of oligomerized olefins.

4. The method of claim 1, wherein the oligomerized olefinic feed comprises a majority of C12 olefins.

5. The method of claim 1, wherein the method comprises (i) a fractionating step carried out before the hydrogenating step, or after the hydrogenating step or both, (ii) the method comprises three hydrogenation stages, or (iii) both (i) and (ii).

6. The method of claim 1, wherein the fluid has an initial boiling point and a final boiling point in the range of from 150 to 230° C., and/or wherein the fluid has a boiling range below 90° C.

7. The method of claim 1, wherein the fluid contains more than 90% by weight of paraffins.

8. The method of claim 1, wherein the fluid contains more than 85% by weight of isoparaffins.

9. The method of claim 1, wherein the fluid contains less than 10% by weight of normal paraffins.

10. The method of claim 1, wherein the fluid contains less than 20 ppm of aromatics by weight.

11. The method of claim 1, wherein the fluid contains less than 10% by weight of naphthenes.

12. The method of claim 1, wherein the fluid thus produced has:
    a naphthenic content below 10% by weight, and
    an isoparaffinic content above 85% by weight, and
    a normal paraffinic content below 10% by weight, and
    an initial boiling point and a final boiling point in the range of from 170 to 260° C., according to ASTM D86, and a boiling range from 10° C. to less than 60° C.

13. The method according to claim 1, wherein the hydrogenation conditions are the following:
    Pressure: about 50 bars;
    Temperature: 135 to 175° C. ;
    Liquid hourly space velocity (LHSV): 0.2 to 1.0 hr$^{-1}$;
    Hydrogen treat rate: 60 to 200 Nm$^3$/ton of feed.

14. A method comprising:
    a step of catalytically hydrogenating a feed comprising more than 85% by weight of oligomerized olefins, at a temperature from 115 to 195° C., at a pressure from 30 to 70 bar and at a liquid hourly space velocity (LHSV) from 0.1 to 3.0 hr$^{-1}$, in order to obtain a fluid having a boiling point in the range of from 150 to 260° C. and comprising more than 80% by weight of isoparaffins and less than 50 ppm of aromatics, wherein the catalyst is a nickel-based catalyst supported on an alumina carrier, wherein the oligomerized olefinic feed is selected from tetrameric propylene cuts, and
    a step of using the fluid as industrial solvent, cleaning solvent, solvent for resins, adhesive, solvent for polymerization, printing ink, metal working fluid, cutting fluid, rolling oil, EDM fluid, coating fluid and paint composition, cupping, protection fluid, hand soap, household product, aerosol, product for photocopiers, odorless fuel for oil stoves, or fluid intended for cosmetic formulations.

15. A method for the preparation of a fluid having an initial boiling point and a final boiling point in the range of from 150 to 260° C., a boiling range of at least 10° C. and comprising more than 80% by weight of isoparaffins and less than 50 ppm of aromatics and having a bromine index of less than 1 mg/Br/100 g of fluid, comprising the step of catalytically hydrogenating a feed comprising more than 85% by weight of oligomerized olefins, at a temperature from 115 to 195° C., at a pressure from 30 to 70 bar and a liquid hourly space velocity (LHSV) from 0.1 to 3 hr$^{-1}$, wherein the oligomerized olefinic feed is selected from tetrameric propylene cuts.

* * * * *